US00PP11753P2

(12) United States Plant Patent
Jonkers

(10) Patent No.: US PP11,753 P2
(45) Date of Patent: Jan. 30, 2001

(54) IMPATIENS PLANT NAMED 'FIFY RED'

(75) Inventor: J. B. (Hanneke) Jonkers, Hoorn (NL)

(73) Assignee: Goldsmith Plants, Inc., Gilroy, CA (US)

( * ) Notice: Under 35 U.S.C. 154(b), the term of this patent shall be extended for 0 days.

(21) Appl. No.: 09/078,661

(22) Filed: May 14, 1998

(51) Int. Cl.[7] ..... A01H 5/00

(52) U.S. Cl. ..... Plt./317

(58) Field of Search ..... Plt./317

(56) References Cited

PUBLICATIONS

GTITM UPOVROM Citation for 'Fify Red' as per QZ PBR 961357; Dec. 9, 1996.*

* cited by examiner

*Primary Examiner*—Howard J. Locker
*Assistant Examiner*—Kent L. Bell
(74) *Attorney, Agent, or Firm*—Rothwell, Figg, Ernst & Kurz

(57) ABSTRACT

A new and distinct cultivar of Impatiens plant, and named 'Fify Red' is provided. 'Fify Red' is distinct in its red flower color, small slightly cup shaped flowers, early flowering and small-leafed basal branching growth habit.

1 Drawing Sheet

BACKGROUND OF THE NEW PLANT

Figure 1:
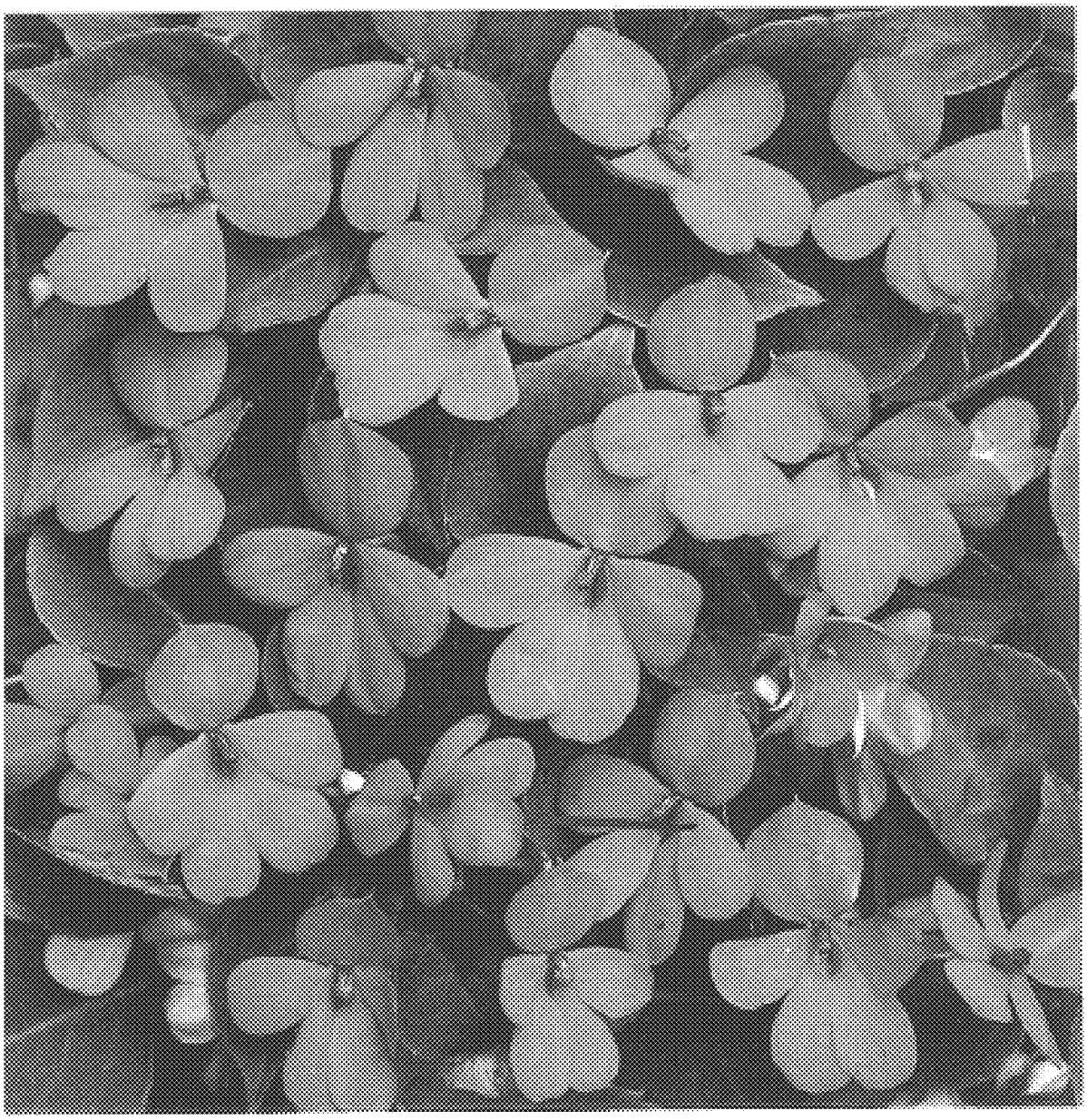

The present invention comprises a new and distinct cultivar of impatiens, botanically known as *Impatiens walleriana,* and hereinafter referred to by the cultivar name 'Fify Red', and is characterized by the following combinations of repeatedly observed traits:

1. Very free flowering,
2. small, single, slightly cup shaped flowers,
3. basal branching with small leaves, and
4. early flowering.

Asexual reproduction of this cultivar by stem cuttings taken during November, 1996, at Andijk, The Netherlands, has demonstrated that the characteristics of the new cultivar as herein described are firmly fixed and are retained through successive generations of such asexual propagation, such reproduction establishing that the plant does in fact maintain the characteristics described in successive generations. The female parent (i.e., the seed parent) was an *Impatiens walleriana* named IN-1444-1 (unpatented) and the male parent (i.e., pollen parent) was an *Impatiens walleriana* named IN-1437-3 (unpatented). The cross was made in 1995 and the seedling was selected in 1996.

This new cultivar has been identified as Impatiens 'Fify Red'. It is possible that other identification will be adopted in the trade, but the name selected will serve for the purposes hereof.

DESCRIPTION OF THE PHOTOGRAPH

This new impatiens plant is illustrated by the accompanying photographic drawing which shows blooms, buds, and foliage of the plant in full color, the colors shown being as true as can be reasonably obtained by conventional photographic procedures.

FIG. 1 shows flowers and foliage of the new plant;

DESCRIPTION OF THE NEW CULTIVAR

The following observations and measurements describe plants grown outside in the field in Andijk, The Netherlands.

Measurements were recorded in August, 1997, on plants approximately 14 weeks old. Fully developed organs were used for measurements and color descriptions, unless otherwise indicated. Color references are made to the R.H.S. Colour Chart of The Royal Horticultural Society, London, England, except where general color terms of ordinary significance are used.

'Fify Red' has not been observed under all possible environmental conditions. The phenotype may vary with variations in environment and horticultural practices, such as temperature, light intensity, day length, fertilization and propagation procedure, without any change in genotype.

Parentage:

*Female parent.*—*Impatiens walleriana* IN-1444-1 (unpatented).

*Male parent.*—*Impatiens walleriana* IN-1437-3 (unpatented).

Propagation:

*Type cutting.*—Stem (internodal) cutting with two nodes and attached leaves.

*Time to initiate roots.*—10–14 days at 70–75 degrees F. with a fully developed root mass at 21 days.

*Rooting habit.*—Fibrous, branching, adventitious root system.

Plant Description:

*Form.*—Upright.

*Growth habit.*—Upright branching plant habit with upper leaves and flowers produced in whorls. When grown in a 4 inch pot for 10–12 weeks the height is approximately 3–4 inches and the width is approximately 4 inches.

*Foliage description.*—Leaves are simple. Lower leaf arrangement is alternate with upper leaves arranged in whorls of 5. Leaf shape is lanceolate to elliptic with acute apex and acute base. Leaf size is 3 cm×2 cm. Leaf margin is crenate with ciliation. Leaf surface is glabrous. Leaf color is green. The upper surface is yellow-green group 147A. Under surface is yellow-green group 147B with purple mottling. Venation is pinnate.

*Petiole.*—Petiole length is 2 cm; and diameter is 0.2 cm; Color is yellow-green 147C.

Flower Description:

*Flowering habit.*—Rooted cutting to full flowering plant in six weeks. Indeterminate, flowering continuously. Flowers develop in the upper leaf axils.

*Natural flowering season.*—Flowers continuously throughout the year.

*Flowers borne.*—Singly on pedicels which are yellow-green 145A and 1–1.5 cm long in clusters of 2–7 flowers with a peduncle color of yellow-green 145A and length of 1–1.5 cm long.

*Spur.*—Short spurred; length is 3.5 cm; color is 51C.

*Buds.*—Buds are oval-shaped at first color 45B; size is 0.8 cm×0.5 cm.

*Quantity of flowers.*—Floriferous. Each axillary cluster of 2–7 flowers developing progressively from the leaf whorls so that buds as well as mature flowers are visible at the same time in large numbers.

*Petals.*—Number of petals 5, with all petals overlapping consisting of 1 round petal approximately 1.2 cm and 4 oval petals approximately 0.8 cm length and 0.5 cm width. Top three petals are slightly cupped.

*Flower color.*—Upper surface: Red group 45B. Lower surface: Red group 47D.

*Flower size.*—Approximately 2.5 cm wide and 2 cm long.

*Reproductive organs.*—Complete pistil, anthers as cap over the pistil dropping off when flower ages. No pollen.

DISEASE AND INSECT RESISTANCE

No known susceptibility to diseases or insects noted to date.

COMPARISON WITH THE KNOWN CULTIVARS

When 'Fify Red' is compared to Impatiens 'Red Chico' (unpatented), it is found that 'Fify Red' exhibits a more vigorous plant habit and is also more floriferous.

When 'Fify Red' is compared to the IN-1444-1 and IN-1437-3, the parental cultivars, the flower size and plant habit are quite different. 'Fify Red' has a smaller flower size than either parental cultivars and 'Fify Red' also has a more compact plant habit than either of the parents.

I claim:

1. A new and distinct cultivar of Impatiens plant named 'Fify Red', substantially as described and illustrated herein, characterized particularly as to novelty by its red flower color, small, slightly cup shaped flowers, early flowering and small-leafed basal branching growth habit.

* * * * *